(12) United States Patent
Urich et al.

(10) Patent No.: US 10,596,033 B2
(45) Date of Patent: *Mar. 24, 2020

(54) PHACOEMULSIFICATION ULTRASONIC DEVICE SWITCHING BETWEEN DIFFERENT OPERATIONAL MODES

(71) Applicants: Alex Urich, Mission Viejo, CA (US); Armand Maaskamp, Napa, CA (US); Ryan Maaskamp, San Francisco, CA (US)

(72) Inventors: Alex Urich, Mission Viejo, CA (US); Armand Maaskamp, Napa, CA (US); Ryan Maaskamp, San Francisco, CA (US)

(*) Notice: Subject to any disclaimer, the term of this patent is extended or adjusted under 35 U.S.C. 154(b) by 845 days.

This patent is subject to a terminal disclaimer.

(21) Appl. No.: 14/517,798

(22) Filed: Oct. 17, 2014

(65) Prior Publication Data
US 2015/0045806 A1 Feb. 12, 2015

Related U.S. Application Data

(63) Continuation-in-part of application No. 13/430,633, filed on Mar. 26, 2012, now Pat. No. 9,216,035.

(51) Int. Cl.
*A61F 9/007* (2006.01)
*A61M 1/00* (2006.01)
(Continued)

(52) U.S. Cl.
CPC ....... *A61F 9/00745* (2013.01); *A61M 1/0064* (2013.01); *A61B 2017/00146* (2013.01); *A61B 2017/22018* (2013.01); *A61B 2017/320084* (2013.01); *A61F 2250/0095* (2013.01); *A61M 2202/0014* (2013.01); *A61M 2202/09* (2013.01); *A61M 2210/0612* (2013.01)

(58) Field of Classification Search
CPC ........ A61F 9/00745; A61F 2250/0095; A61M 1/0064; A61M 2210/0612;
(Continued)

(56) References Cited

U.S. PATENT DOCUMENTS

3,990,452 A * 11/1976 Murry .............. A61B 17/22012
606/169
5,112,300 A * 5/1992 Ureche ............... A61F 9/00745
310/323.18
(Continued)

*Primary Examiner* — Phong Son H Dang
(74) *Attorney, Agent, or Firm* — Kenneth Altshuler (57) ABSTRACT

A surgical instrument and method, for example to accomplish phacoemulsification, are disclosed. The surgical instrument includes a handpiece that includes a piezoelectric transducer. A hollow titanium needle having a substantially cylindrical portion and a free distal tip is attached to the handpiece by way of a threaded supported end structure. The piezoelectric transducer is driven by a circuit to periodically expand and contract at a high-ultrasound frequency that rings the hollow titanium needle with a high-ultrasonic frequency standing wave having a node of minimum amplitude residing in the substantially cylindrical portion between the supported end structure and the free distal tip, and to periodically expand and contract at an ultrasound frequency that rings the hollow titanium needle with an ultrasonic frequency standing wave, the circuit adapted to between the high-ultrasonic frequency and the ultrasonic frequency.

20 Claims, 9 Drawing Sheets

(51) Int. Cl.
*A61B 17/22* (2006.01)
*A61B 17/00* (2006.01)
*A61B 17/32* (2006.01)

(58) Field of Classification Search
CPC ...... A61M 2202/0014; A61M 2202/09; A61B 2017/00146; A61B 2017/22018; A61B 2017/320084
See application file for complete search history.

(56) References Cited

U.S. PATENT DOCUMENTS

| | | | | |
|---|---|---|---|---|
| 5,180,363 A | * | 1/1993 | Idemoto | B06B 3/00 604/22 |
| 5,213,569 A | | 5/1993 | Davis | |
| 5,261,922 A | * | 11/1993 | Hood | A61B 17/320068 606/167 |
| 5,695,510 A | * | 12/1997 | Hood | A61B 17/320068 606/169 |
| 6,733,451 B2 | * | 5/2004 | Rabiner | A61B 17/22012 600/439 |
| 7,794,414 B2 | * | 9/2010 | Rabiner | A61B 17/22012 601/2 |
| 2005/0234473 A1 | * | 10/2005 | Zacharias | A61F 9/00745 606/107 |
| 2006/0235306 A1 | * | 10/2006 | Cotter | A61B 17/1604 600/459 |
| 2008/0294087 A1 | * | 11/2008 | Steen | A61F 9/00745 604/22 |
| 2009/0069712 A1 | * | 3/2009 | Mulvihill | A61B 10/025 600/564 |

* cited by examiner

PHACOEMULSIFICATION ULTRASONIC DEVICE SWITCHING BETWEEN DIFFERENT OPERATIONAL MODES

CROSS-REFERENCE TO RELATED APPLICATIONS

This application is a Continuation-In-Part application claiming the priority to and the benefit of U.S. patent application Ser. No. 13/430,633 entitled SURGICAL INSTRUMENT RINGING A TITANIUM NEEDLE WITH A NODE OF MINIMUM AMPLITUDE IN A SUBSTANTIALLY CYLINDRICAL PORTION OF THE NEEDLE, filed on Mar. 26, 2012, the entire disclosure of which is hereby incorporated by reference.

FIELD OF THE INVENTION

The present invention relates generally to the field of medical devices used in surgery, and more particularly to tools and methods used in phacoemulsification procedures.

BACKGROUND

Needles that are actuated at ultrasonic frequencies may be used in various contemporary surgical procedures. For example, the lens of a human eye may develop a cataracteous condition that affects a patient's vision. Cataracteous lenses are sometimes removed and replaced in a procedure commonly referred to as phacoemulsification. Phacoemulsification procedures are typically performed with a handpiece that actuates a needle at ultrasonic frequencies. The needle is inserted through an incision in the cornea up to a desired insertion depth, and then ultrasonic actuation at a specific frequency is used to break the lens within the lens capsule of the eye. The broken lens may be removed through an aspiration line that is coupled to the hand piece, drawing irrigation fluid and aspirated tissue from a hollow passage through the needle. It is to improvements in ultrasonic actuation of a phacoemulsification needle that embodiments of the present invention are directed.

SUMMARY

The present invention is directed to embodiments of a phacoemulsification device that can switch between two different ultrasonic frequencies, such as one defined as "high-ultrasonic frequency" higher than 100 KHz and the other defined as "ultrasonic frequency" lower than 100 KHz, for example. The two frequencies produce different surgical effects when used to emulsify a cataracteous lens.

Certain embodiments of the present invention can therefore comprise a surgical instrument and method to accomplish phacoemulsification are disclosed. The surgical instrument generally possesses a handpiece (also called an ultrasonic horn) that includes a piezoelectric transducer, a hollow titanium needle having a free distal tip and a supported end structure that is attached to the handpiece, the supported end structure includes external threads that mate with internal threads in the handpiece, the hollow titanium needle having a substantially cylindrical portion between the supported end structure and the free distal tip and a circuit that drives the piezoelectric transducer. The piezoelectric transducer can be made to periodically expand and contract at a high-ultrasound frequency that rings the hollow titanium needle with a standing wave having a node of minimum amplitude residing in the substantially cylindrical portion between the supported end structure and the free distal tip. The piezoelectric transducer can further be made to periodically expand and contract at an ultrasound frequency that rings the hollow titanium needle with an ultrasonic frequency standing wave. The circuit is adapted to modulate between the high-ultrasonic frequency and the ultrasonic frequency.

Other embodiments of the present invention can therefore comprise a method to drive oscillations in a surgical instrument for phacoemulsification, the method comprising: providing a handpiece that includes a piezoelectric transducer, a hollow titanium needle having a free distal tip and a supported end structure that is attached to the handpiece, the hollow titanium needle possessing a length being defined along a longitudinal axis of the hollow titanium needle; energizing the piezoelectric transducer to periodically longitudinally expand and longitudinally contract along the length at an ultrasonic driving frequency that rings the hollow titanium needle with an ultrasonic standing wave that is characterized by longitudinal expansion and longitudinal contraction of the hollow titanium needle; and energizing the piezoelectric transducer to periodically longitudinally expand and longitudinally contract along the length at a high-ultrasonic driving frequency that rings the hollow titanium needle with a high-ultrasonic standing wave that is characterized by longitudinal expansion and longitudinal contraction of the hollow titanium needle, the standing wave having a node of minimum amplitude along the length of the hollow titanium needle.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving eye surgery.

Figure 1:
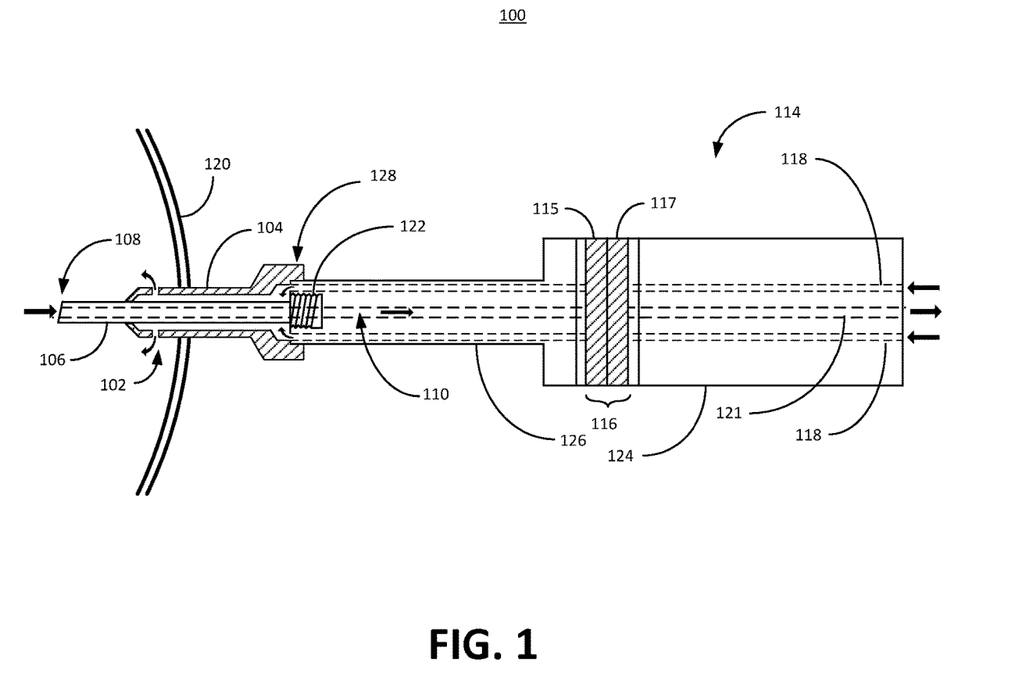
FIG. 1 illustratively depicts an embodiment of a phacoemulsification device inserted in an eye consistent with embodiments of the present invention.

To illustrate an exemplary environment in which preferred embodiments of the present invention can be practiced, FIG. 1 depicts an embodiment of a phacoemulsification device 100 inserted in an eye 120 consistent with embodiments of the present invention. As depicted, the phacoemulsification device 100 generally comprises a handpiece 114, a hollow aspiration needle 106 extending from the handpiece 114, an irrigation sleeve 104 that surrounds a portion of the aspiration needle 106 (also known as a phacoemulsification needle), and at least one irrigation port 102 extending through the irrigation sleeve 104.

During an ultrasonic phacoemulsification surgical procedure, a cataracteous lens may be broken into particles by the combined cutting action of an ultrasonically vibrating needle tip 108 and cavitation effects. The vibration may provide penetration of the needle 106 into lens tissue, while the cavitation may help emulsify or disintegrate lens tissue into small particles that can be aspirated through a narrow tube 110 in the hollow aspiration needle 106. Cavitation can occur because the hollow phacoemulsification needle 106 compresses and expands along its longitudinal axis, thus generating longitudinal waves in the surrounding fluid. Unlike torsional and shear waves, longitudinal waves may propagate well in fluids.

As further depicted in FIG. 1, the handpiece 114 includes a back cylinder 124 and a front cylinder 126, a piezoelectric transducer 116 comprising a pair of piezoelectric crystals 115 and 117 connected through a central bolt (not shown), irrigation pathways 118 and an aspiration pathway 121. The hollow titanium needle 106 is attached to the handpiece 114 at the supported end 128. The supported end 128 generally comprises a supported end structure 122 that includes external threads that mate with internal threads in the handpiece 114. The hollow titanium needle 106 possesses a substantially cylindrical portion between the supported end structure 122 and the free distal tip 108.

One embodiment of the handpiece 114 contemplates the back cylinder 124 possessing an outer diameter that is preferably in the range 9.5 mm to 13 mm. The back cylinder 124 may be generally comprised of stainless steel, for example. The handpiece 114 may also optionally include a front cylinder 126 that may have a front cylinder outer diameter that is preferably in the range 3.5 mm to 6.5 mm. In this case, the piezoelectric transducer 116 is preferably disposed between the back cylinder 124 and the front cylinder 126.

Figure 2:
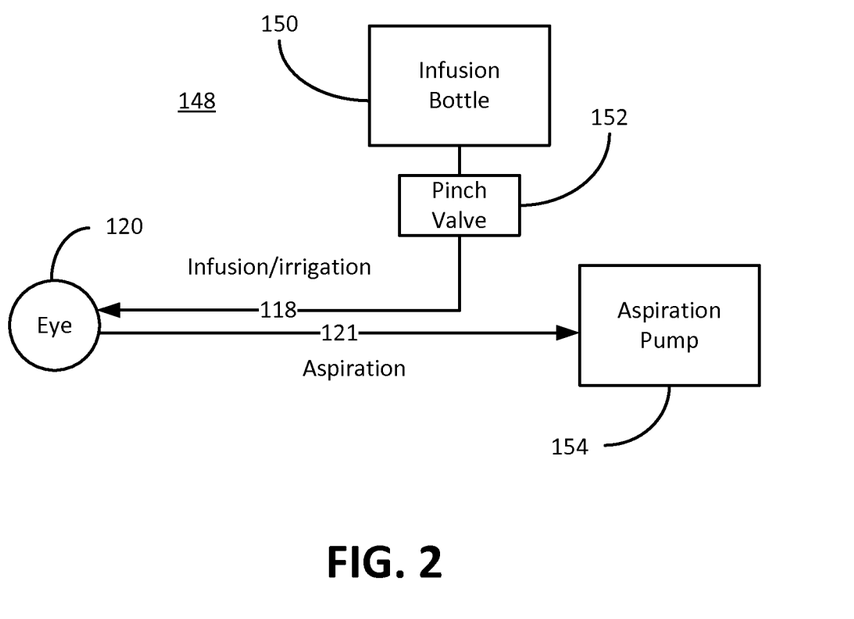
FIG. 2 is a block diagram of a phacoemulsification system embodiment consistent with embodiments of the present invention.

With reference to FIG. 2 in conjunction with FIG. 1, shown therein is a block diagram of a phacoemulsification system embodiment 148. As shown, the phacoemulsification system 148 includes an infusion bottle 150 of balanced salt solution generally positioned between 100 cm to 130 cm above the eye 120 (or to a level that gravitationally provides balanced intraocular pressure (IOP) in the eye 120, which is generally between 10 mm Hg and 20 mm Hg and averages to 15.5 mm Hg in a human eye. During a cataract surgery, a surgeon tries to keep the IOP above 20 mm Hg, especially after a vacuum surge. Osmotically balanced salt solution is compatible with the ocular fluid in the eye 120. The system 148 further provides a pinch valve 152 that opens and closes an infusion/irrigation pathway 118 to the eye 120. An aspiration pump 154 is adapted to suck emulsified lens material (ocular material) from the eye 120 through the hollow opening in the distal tip 108 of the hollow titanium needle 106. During a phacoemulsification procedure, the aspiration needle 106 is inserted through an incision in the anterior chamber of the eye 120 (at the cornea) up to and including the irrigation port 102. One embodiment contemplates the hollow titanium needle 106 vibrated at an ultrasonic frequency or at a high-ultrasonic frequency to break up (emulsify) lens material in the eye 106. Ultrasonic frequency used herein is defined to be a frequency between 20 KHz and 100 KHz, and high-ultrasonic frequency is defined to be a frequency above 100 KHz. The small pieces of the emulsified lens material are sucked through the hollow aspiration needle 106 away from the eye 120 along the aspiration pathway 121 by way of a vacuum generated by the aspiration pump 154. The aspiration pump 154 is adapted to pull (vacuum) a volume of emulsified lens material at a particular rate from the eye 120. Generally, the aspiration rate is approximately 25 to 50 cc of fluid/minute. Irrigation fluid replaces the removed lens material (at the same particular rate of aspirated lens material) by way of gravity from the infusion bottle 150 that is raised at an appropriate distance above the eye 120 to maintain IOP. The irrigation fluid flows (is discharged) into the inside of the eye 120 through the irrigation port 102 that is inside of the eye 120. In other words, the irrigation fluid replaces the lens material at the rate at which the lens material is removed from the eye 120 to maintain appropriate IOP, thus avoiding collapse of the anterior chamber of the eye 120. Hence, the irrigation flow rate into the eye 120 essentially equals the aspiration flow rate from the eye 120. The word essentially is used here to indicate that at some level there flow rate is not exactly equal, but for all intents and purposes is more or less equal. The irrigation port 102 is a pathway into the irrigation sleeve 104, whereby irrigation fluid passes from the irrigation sleeve 104 out the irrigation port 102 into the eye 120. The irrigation sleeve 104 is spaced apart from the hollow titanium needle 106 to form an irrigation pathway 118. The irrigation pathway 118 extends from the infusion bottle 150, through the handpiece 114 to the irrigation port 102.

The effectiveness of a surgical instrument for phacoemulsification depends on the rate at which tissue is removed, which may be substantially affected by cavitation since cavitation may reduce partial or total occlusions of the hollow titanium needle 106. On the other hand, a particle engaged with the hollow titanium needle 106 by vacuum may partially disintegrate if the ultrasonic energy causes high cavitation. In this case, the surgeon may lose the particle and additional maneuvers may be necessary to reengage. Retention of tissue particles in engagement with the hollow titanium needle 106 is desirable and may be referred to as "followablity." To improve followability, reduced cavitation during phacoemulsification may be advantageous.

One way to reduce cavitation is to excite the hollow titanium needle 106 to vibrate torsionally rather than longitudinally, so that the needle tip alternately rotates clockwise and counter-clockwise in relation to its longitudinal axis. Torsional vibrations do not readily propagate as waves in fluid, so that cavitation effects are substantially reduced. However a needle tip 108 that is vibrating purely torsionally may too easily core into the lens material without sufficient disintegration of tissue into particles, which, in turn, may too frequently lead to total occlusions in the hollow titanium needle 106.

According to one of the embodiments of the present invention disclosed herein, followability may be enhanced by longitudinally ringing a hollow titanium needle 106 at a carefully selected and substantially higher frequency than has been used previously for phacoemulsification. Most preferably, the ringing frequency is chosen so that the phacoemulsification needle length corresponds to approximately three quarter vibration wavelengths. Such a higher ultrasonic frequency, in combination with the proper length of the hollow titanium needle 106, may lead to reduced heating of tissue at the incision in the cornea, this is considered a "cold" needle, and may generate larger numbers but smaller sized cavitation bubbles per unit volume. The energy delivered by a cavitation bubble is related to the bubble radius, which in turn is inversely related to the frequency of vibration. For example, a bubble size generated by a 40 KHz wave may be approximately 41 µm, while being only 7.6 µm at 215 KHz. When more and smaller bubbles are generated, cavitation patterns may be more uniformly distributed over the cutting area, which, in turn, may enhance followablity relative to phacoemulsification needle's operating with conventional longitudinal ultrasonic vibrations.

Figure 3:
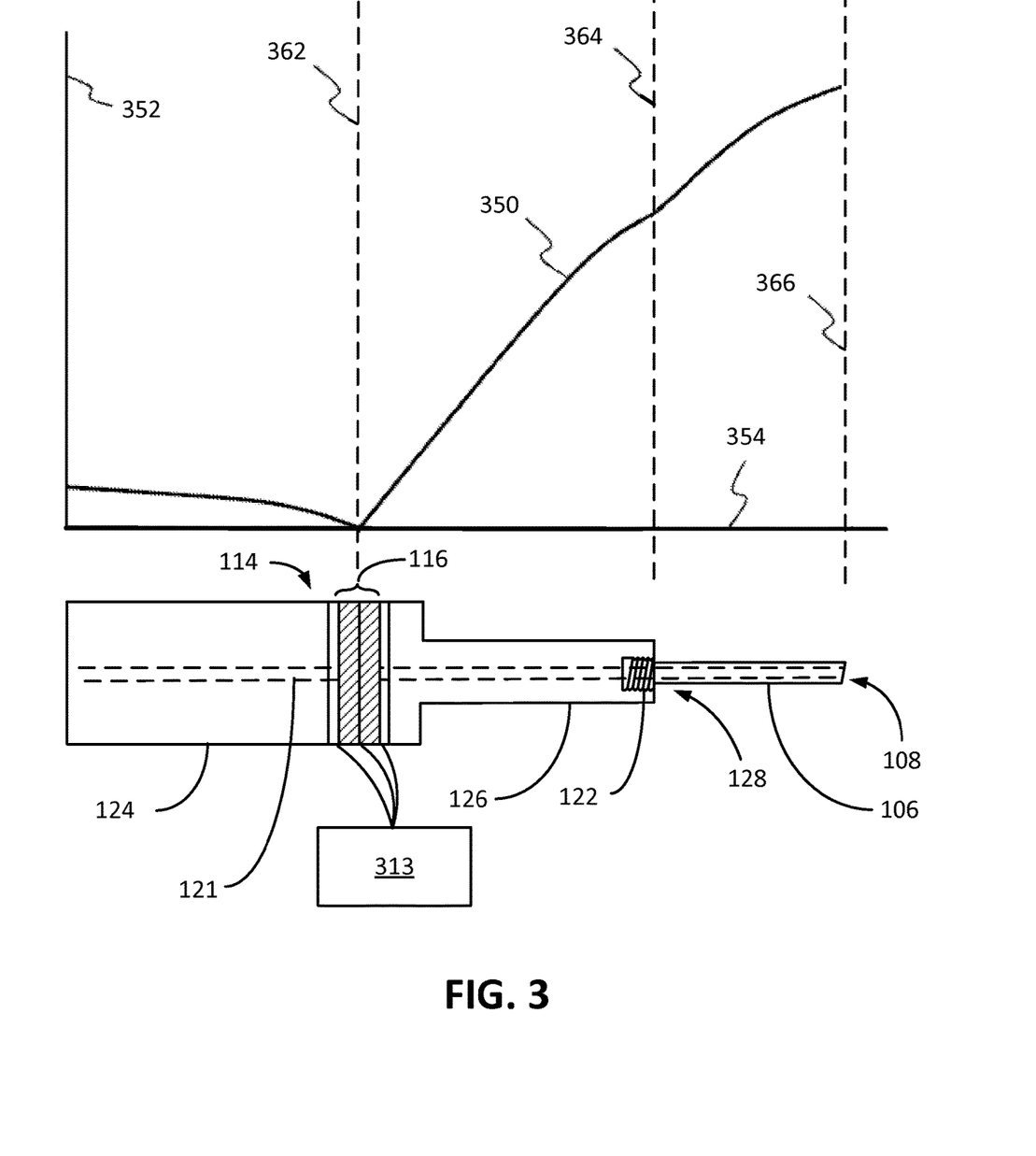
FIG. 3 illustratively depicts an embodiment of a handpiece and hollow titanium needle operating at an ultrasonic frequency against a graphical plot of the ultrasonic frequency response consistent with embodiments of the present invention.

FIG. 3 depicts an embodiment of a handpiece 114 for longitudinal vibration of the hollow titanium phacoemulsification needle 106, operating at an ultrasonic frequency between 20 KHz and 100 KHz. The handpiece 114 includes a back cylinder 124 and a front cylinder 126 compressing a pair of piezoelectric crystals 115, 117 sandwiched via a central bolt (not shown). Some embodiments contemplate four or six piezoelectric crystals or more. The piezoelectric crystals 115, 117 are driven by a circuit 313 that provides an oscillating voltage to the piezoelectric transducer 116. The wavelength λ of a longitudinally ringing structure is given by the formula λ=c/f where c is the speed of sound through the structure's material and f is the frequency of operation. Titanium material exhibits a speed of sound that is approximately 4,876,800 mm/sec. Accordingly, the hollow titanium needle 106 longitudinally vibrating at a frequency of 40 KHz (40000 Hz) has a wavelength of (4,876,800 mm/s)/(40,000 Hz)=122 mm.

In FIG. 3, the combined length of the front and back cylinders 126, 124 is approximately ½ wavelength during conventional ultrasonic operation, with a node of zero vibration amplitude at a location 362 at the interface between the two piezoelectric crystals 115, 117. For that reason, the handpiece 114 may be referred to as a "half-wavelength horn."

Figure 3A:
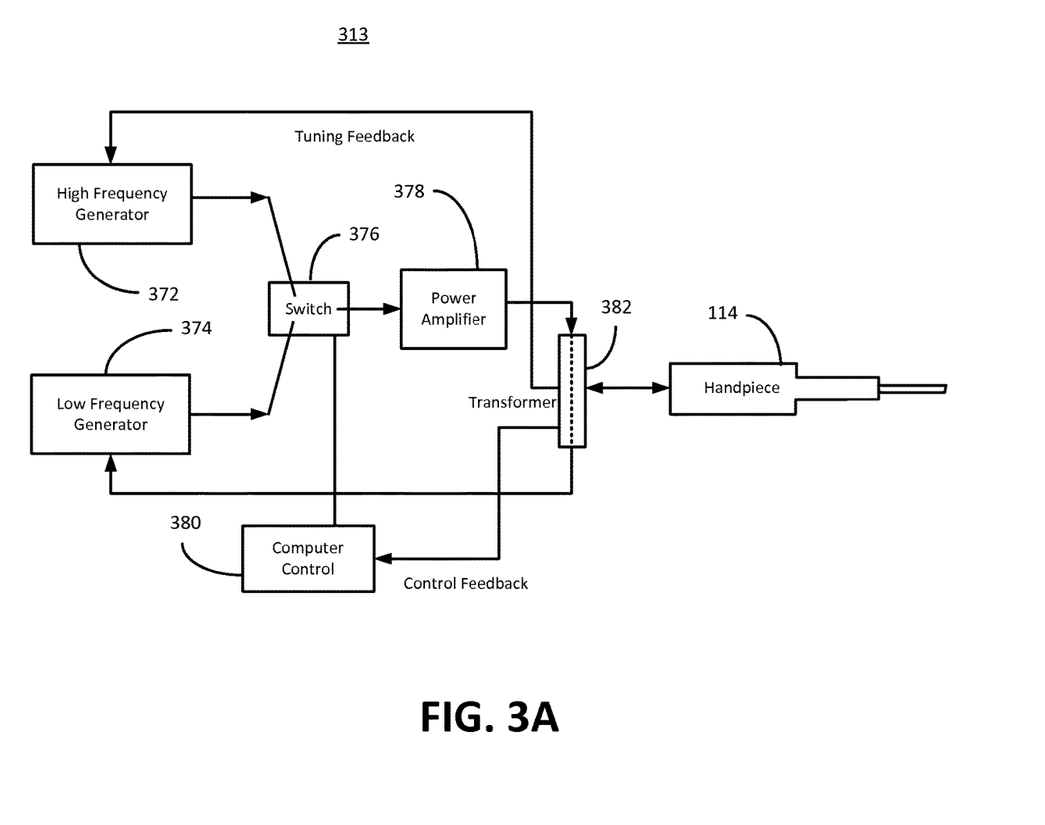
FIG. 3A is a block diagram illustratively depicting an embodiment of a control feedback circuit consistent with embodiments of the present invention.

FIG. 3A is a block diagram illustratively depicting an embodiment of a control feedback circuit 313 that provides an oscillating voltage to the piezoelectric transducer 116. Generally shown is a high-frequency generator 372 that provides high-ultrasonic frequency voltage input to the piezoelectric transducer 116 in the handpiece 114 and a lower frequency generator 374 that provides ultrasonic frequency voltage input to the piezoelectric transducer 116 in the handpiece 114 via the switch 376, power amplifier 378 and a transformer 382. More specifically, a computer control unit 380 sends signals to modulate input from either the high frequency generator 372 or the low frequency generator 374, wherein that signal (from one of the generators 372, 374) passes through the switch 376 where it is amplified by the power amplifier 376 and then translated to the two piezoelectric crystals 115, 117 via the transformer 382 to drive the hollow titanium needle 106 with the desired frequency wave. This control feedback circuit 313 is arranged to detect slight impedance changes of the transducer 116, thus being capable to sensing increased loading to the system, e.g., an engaged particle occluding the hollow titanium needle 106, causing the computer controller 380 to toggle the switch 376 (or vice versa if the particle is no longer engaged with the hollow titanium needle 106).

FIG. 3 is not drawn to scale, so that the hollow titanium phacoemulsification needle 106 may be more clearly depicted as a hollow cylinder. The hollow titanium needle 106 can be attached to the handpiece 114 using threads (not shown). One embodiment contemplates the length of the hollow titanium needle 106 having a small cross-sectional area with a length that is less than ¼ wavelength (30.5 mm at 40 kHz), for example 17 mm. The mass of the hollow titanium needle 106 is also small when compared with the mass of the handpiece 114. Consequently the hollow titanium needle 106 does not dramatically change the dynamic resonance characteristics of the handpiece 114. As discussed previously, the hollow titanium needle 106 includes a narrow tubular passage 121 there through. The tubular passage 121 continues through the entire handpiece 114 so that fluid and tissue can be aspirated through the hollow titanium needle 106 to an aspiration tube that is connected to the handpiece 114. The aspiration tube is linked to a pump 154 that provides sub-ambient pressure to the narrow tubular passage 121 to suck aspirated material from the eye 120.

The cross sectional area of the front cylinder 126 of the handpiece 114 is smaller than the cross section area of the back cylinder 124, in order to provide displacement magnification as shown in the graph 350 in the upper portion of FIG. 3. Specifically the displacement at the rightmost extent 364 of the front cylinder 126 may be about 20 times the displacement at the leftmost edge 352 of the rear cylinder 124. Note that the vertical axis 352 of the graph 350 represents displacement amplitude (longitudinal compression and expansion increasing upwards). The horizontal axis 354 of the graph 350 represents the longitudinal coordinate along the length of the handpiece 114 and hollow titanium needle 106. Longitudinal strain in the hollow titanium needle 106 marginally increases displacement plotted in graph 350, though the entire hollow titanium needle 106 longitudinally translates. For example, the displacement at the location 366 of the distal end 108 of the hollow titanium needle 118 is somewhat greater than the displacement at the rightmost extent 364 of the front cylinder 126. Note that there is no location of zero vibration (i.e. nodal point) along the length of the hollow titanium needle 106.

One embodiment contemplates the hollow titanium needle 106 being substantially cylindrical, with an outer diameter in the range 0.5 mm to 1.5 mm and a length in the range 12 mm to 37 mm, the length being defined along a longitudinal axis of the hollow titanium needle 106 (i.e. parallel to graph axis 354). In this context "cylindrical" does not necessarily mean cylindrical with a circular or annular cross section. Rather, any closed hollow extruded shape may be used (e.g. a closed hollow square cross-section). However, an annular cross-section having circular inner and outer peripheries may be preferred for manufacturability.

Figure 4:
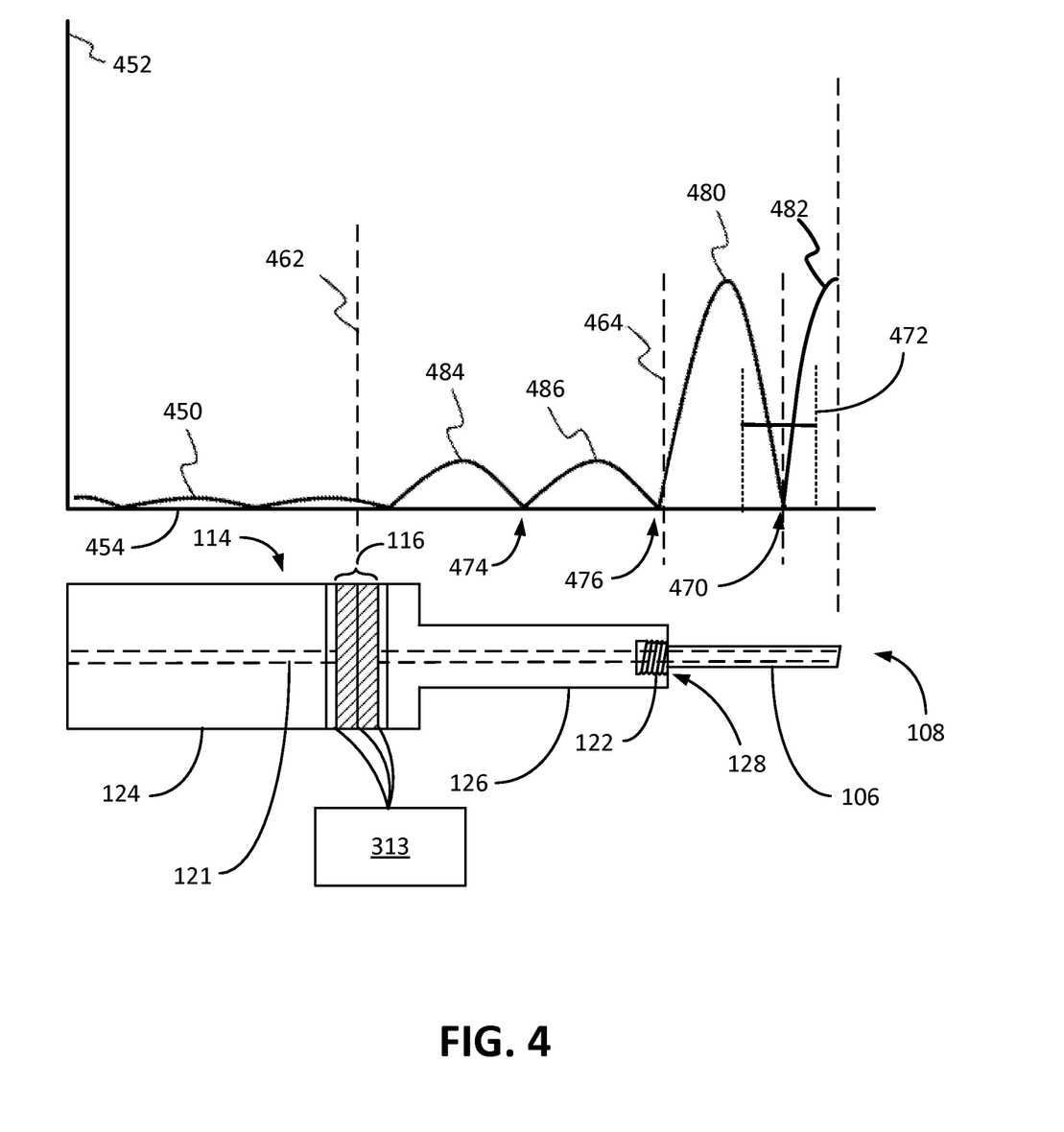
FIG. 4 illustratively depicts an embodiment of a handpiece and hollow titanium needle operating at a high-ultrasonic frequency against a graphical plot of the high-ultrasonic frequency response consistent with embodiments of the present invention.

FIG. 4 depicts an embodiment of the surgical instrument of FIG. 3 whereby the handpiece 114 is ringing the hollow titanium needle 106 at a high-ultrasonic frequency, above 100 KHz. As previously described, the handpiece 114 includes a piezoelectric transducer 116, wherein the transducer 116 comprises a sandwich structure of two piezoelectric elements 115, 117 which meet at an interface location 462. The piezoelectric elements 115, 117 may comprise piezoelectric ceramics or crystals, preloaded to be in compression by a bolt in tension, for example.

The front cylinder 126 may also be generally comprised by titanium, for example, to match the speed of sound of the hollow titanium needle 106 and thereby reduce acoustic reflections at the interface between the front cylinder 126 and the titanium needle 106.

The surgical instrument depicted in FIG. 4 includes a circuit 313 that provides an oscillating voltage to the piezoelectric transducer 116 in the handpiece 114, the voltage oscillating at a driving frequency that rings the hollow titanium needle 106 at a frequency in the high-ultrasonic range with a standing wave that is characterized by longitudinal expansion and longitudinal contraction. In certain embodiments, the frequency with which the circuit 313 drives the piezoelectric transducer 116 is preferably in the range 100 KHz to 1000 KHz. For example, the total length of the hollow titanium needle 106 may be approximately 17 mm, and the driving frequency may be approximately 215 KHz. Higher frequencies may introduce additional nodal waves along the length of the titanium needle 106.

Such dimensional ranges and driving frequencies may advantageously result in 3 quarter wavelengths of the longitudinal standing wave lying along the hollow titanium needle 106 if it is a titanium needle of 17 mm total length. This can be verified by referring again to the formula $\lambda=c/f$. Specifically, according to this formula the wavelength of the standing longitudinal wave in a titanium needle would be (4,876,800 mm/s)/215,000 Hz)=22.7 mm. Hence, approximately ¾ wavelengths would lie along a needle length of 17 mm.

An example of the amplitude of the longitudinal expansion and longitudinal contraction causing displacement along the handpiece 114 and the hollow titanium needle 106, according to an embodiment of the present invention, is plotted versus longitudinal position in the graph 450 that appears above the handpiece 114 in FIG. 4. The vertical axis 452 of the graph 450 represents displacement amplitude (increasing upwards). The graph 450 illustratively depicts dimensionless values of the displacement amplitude. The horizontal axis 454 of the graph 450 represents the longitudinal coordinate along the length of the handpiece 114 and the hollow titanium needle 106.

In the embodiment of FIG. 4, the standing wave shown in graph 450 preferably has a distal node of minimum amplitude at a node location 470 on the substantially cylindrical hollow titanium needle 106. That is depicted on the graph 450 as a minimum point at the node location 470. Unlike ultrasonic vibrations in a range under 100 KHz (e.g. like that shown in FIG. 3), the portion of the hollow titanium needle 106 that is most likely to contact the incision in the cornea, may be in a region 472 that includes a minimum node in the standing wave of vibration, and therefore experiences a much lower motion than does the distal tip 108. In certain embodiments, this may advantageously reduce heating of the tissue at and near the incision in the cornea.

Figure 5:
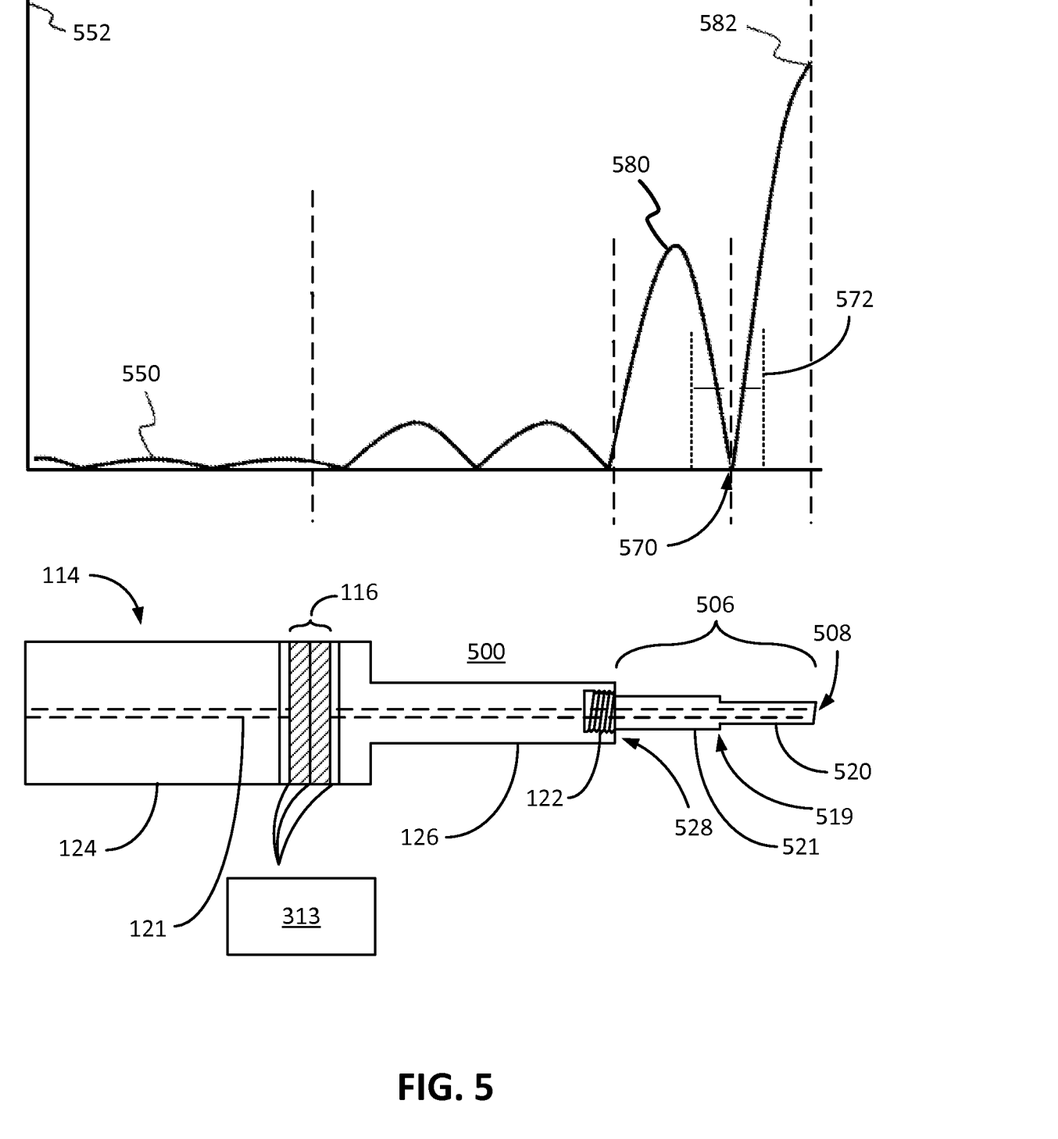
FIG. 5 illustratively depicts an embodiment of a handpiece and hollow titanium needle with a shoulder in the substantially cylindrical portion of the needle consistent with embodiments of the present invention.

One optional embodiment depicted in FIG. 5 contemplates the hollow titanium needle 506 to include a shoulder 519 where the outer diameter of hollow titanium needle 506 changes. The hollow titanium needle 506 includes a first substantially cylindrical portion 520 between the shoulder 519 and the free distal tip 508, and a second substantially cylindrical portion 521 between the shoulder 519 and the supported end 528. In this case, the shoulder 519 is preferably disposed between 5 mm to 8 mm from the free distal tip 508. The outer diameter of the hollow titanium needle 506 is preferably less in the first substantially cylindrical portion 520 than in the second substantially cylindrical portion 521; as such inequality may advantageously amplify the ringing amplitude in the first substantially cylindrical portion 520 as illustratively depicted by the graph 550 when the hollow titanium needle 506 is subjected to a high-ultrasonic frequency. In more detail, there is a distal node of minimum amplitude at a node location 570 on the substantially cylindrical hollow titanium needle 506. Also, in the embodiment of FIG. 5, the standing wave shown in graph 550 may have a distal anti-node 582 of maximum amplitude at the free distal tip 108 (which has a peak higher than the amplitude of the anti-node 580 because the hollow titanium needle 109 possesses the thinner first substantially cylindrical portion 520 in this embodiment), so that high displacement amplitude at the distal tip 108 can enhance tissue penetration by the distal tip 108.

In certain embodiments, including certain embodiments that lack any shoulder 519, the reduced corneal incision heating advantage may be obtained by the distal node of minimum amplitude (at node location 470) being preferably disposed between 5 mm to 8 mm from the free distal tip 108. Although in the embodiment of FIG. 5 the shoulder 519 is depicted as being immediately adjacent the distal node of minimum amplitude (at node location 470), there is no requirement for that, and indeed in certain embodiments it is preferred that they not be at the same longitudinal location. For example, in certain embodiments, it is preferred that the distal node of minimum amplitude (at node location 470) be disposed more distally (to the right in FIG. 5) than the shoulder 519.

In the embodiment of FIG. 4, the standing wave shown in graph 450 has a proximal node of minimum amplitude 476 near or adjacent the supported end 128. That is depicted as a minimum point on the graph 450, just to the left of the location 464. Note that the proximal node of minimum amplitude 476 is not the same as the distal node at node location 470, and it does not serve the same purposes as described for the distal node at node location 470. Also, in the embodiment of FIG. 4, the standing wave shown in graph 450 may have a distal anti-node 482 of maximum amplitude at the free distal tip 108 (which has a peak at essentially the same amplitude as the anti-node 480 because the hollow titanium needle 109 is a constant thickness in this embodiment), so that high displacement amplitude at the distal tip 108 can enhance tissue penetration by the distal tip 108.

Other nodes (e.g. node 474) may exist in the displacement amplitude graph along the front cylinder 126, but these are not the same as the distal node at node location 470, nor do they serve the same purposes as described for the distal node at node location 470. Another anti-node 480 may exist in the substantially cylindrical portion of the hollow titanium needle 106, but it does not serve the same purpose as does the distal anti-node 482 of maximum amplitude at the free distal tip 108. However, in certain embodiments, the existence and location of the anti-node 480 is an expected consequence of the desired placement of the distal node of minimum amplitude at a node location 470 on the substantially cylindrical hollow titanium needle 106 (as described in previous paragraphs). Other anti-nodes (e.g. anti-nodes 484, 486) may exist in the displacement amplitude graph along the front cylinder 126, but these are not the same as the distal anti-node 482 of maximum amplitude at the free distal tip 108, nor do they serve the same purpose as does the distal anti-node 482 of maximum amplitude at the free distal tip 108

Embodiments of the present invention contemplate switching vibrations to the hollow titanium needle 106 between ultrasonic frequency and high-ultrasonic frequency. As previously discussed, at high-ultrasonic frequency (FIG. 4) there is a node of minimum amplitude 470 along the substantially cylindrical portion of the hollow titanium needle 106 between the distal free end 108 and the supported end 128 whereby near or at the distal node of minimum amplitude 470 there is little to no heat generated. This is considered to be a "cold" needle. The circuit 313 is adapted to modulate, or change, the frequency between the ultrasonic frequency and high-ultrasonic frequency.

Certain embodiments contemplate a routine (either in hardware or in software) that causes the circuit 313 to modulate frequencies driving the hollow titanium needle 106 between the ultrasonic frequency and high-ultrasonic frequency after a predetermined time interval. One embodiment envisions the frequency modulating between ultrasonic frequency and high-ultrasonic frequency in a symmetrical amount of time. For example, after every 5 seconds (or some other amount of time) the circuit 313 drives the hollow titanium needle 106 from the ultrasonic frequency to the high-ultrasonic frequency and then back again. Yet another example includes causing the circuit 313 to change from ultrasonic to high-ultrasonic in an asymmetric amount of time, such as for example, 5 seconds (or some other amount of time) at ultrasonic frequency then 3 seconds (or some other amount of time) at high-ultrasonic frequency and then repeat. The predetermined amount of time is envisioned to be set either manually by someone in the operating room or default routines set by the manufacturer, just to name a couple of examples to set a predetermined amount of time. Other certain embodiments contemplate manual intervention to modulate frequencies driving the hollow titanium needle 106 between the ultrasonic frequency and high-ultrasonic frequency. One embodiment envisions a foot pedal or other manually operated switching device (or potentiometer) modulating the frequency between ultrasonic frequency and high-ultrasonic frequency.

Figure 6:
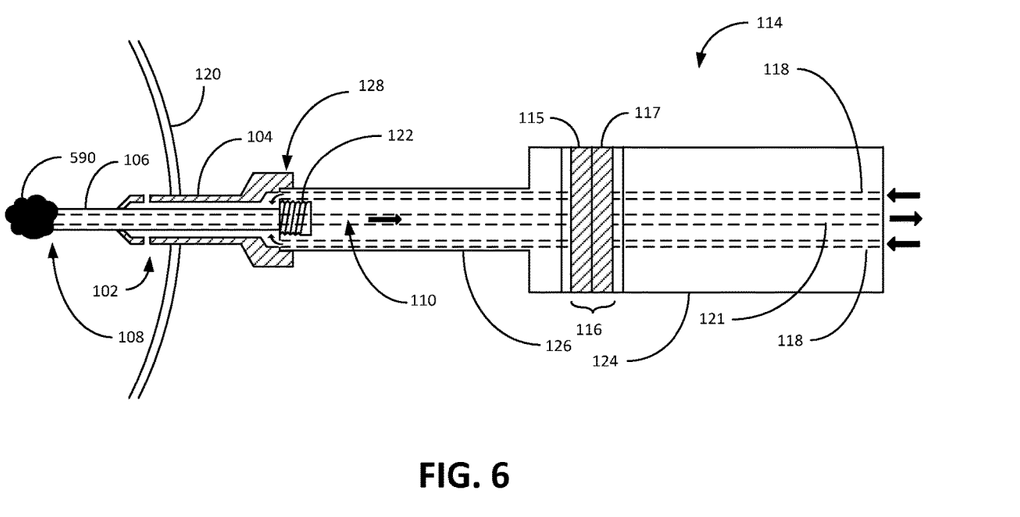
FIG. 6 illustratively depicts an occluding particle obstructing the aspiration pathway at the free distal tip of a hollow titanium needle consistent with embodiments of the present invention.

Yet other certain embodiments contemplate an event during a phacoemulsification procedure that drives the hollow titanium needle 106 to modulate from between the ultrasonic frequency and high-ultrasonic frequency. For example, and with reference to FIG. 6, depicted is a particle 590, such as lens material, that is occluding the aspiration pathway 121 at the free distal tip 108 of the hollow titanium needle 106. When a particle 590 is engaged in such a way, it can decrease flow rate in an aspiration pathway 121. For example, with a peristaltic pump, the aspiration flow rate is always constant. The pump automatically increases vacuum to overcome an increased resistance to flow. If an occlusion (such as from the particle 590) is not cleared by the maximum vacuum the pump can create, the flow drops to zero. Hence, the flow rate is either constant or zero. With a Venturi type pump, the flow rate decreases or increases as a function of pipe resistance, which can be caused by an occlusion (such as from the particle 590). In either situation, the irrigation flow along pathway 118 is reduced or drops to zero to match the pump flow rate in order to maintain proper IOP. A reduction or stoppage of irrigation fluid can cause localized heating at the cornea. In this situation, increasing the frequency of the hollow titanium needle from ultrasonic to high-ultrasonic can reduce localized heating at the incision site of the cornea and can help break up the particle 590 to allow aspiration and irrigation to proceed normally at an unblocked flow rate.

Feedback in the phacoemulsification system 148 to an occlusion or partial occlusion of the aspiration pathway 121 due to a particle 590 can be used to trigger the hollow titanium needle 106 to modulate from the ultrasonic frequency and the high-ultrasonic frequency (or optionally back and forth) to break up the particle 590 and reduce heating at the corneal incision during a phacoemulsification procedure. Some embodiments contemplate using feedback in the phacoemulsification system 148 to identify a particle engaged in an occluding or partial occluding manner includes a diminishing change in aspiration flow rate of ocular material aspirated from an eye 120, a diminishing change in irrigation flow rate of irrigation fluid into the eye 120, an increasing change in aspiration vacuum or how much harder an aspiration pump 154 has to work to aspirate ocular material from the eye 120 increases, or an increase in load to drive the frequency of the hollow titanium needle 106 due to an increased mass of a particle engaged/lodged in or on the hollow titanium needle 106.

Some embodiments contemplate identifying the presence of a particle 590 either occluding or partially occluding the aspiration path 121 based on a diminishing change in aspiration flow rate of the aspirated ocular material from the eye 120. A sensor (not shown) can be located in the infusion/irrigation pathway 118, or elsewhere, to sense a diminished flow rate of aspirated ocular material from the eye 120. Shifting ringing the hollow titanium needle 106 from an ultrasonic frequency to a high-ultrasonic frequency can help break apart an occluding particle 590 and reduce heating at the cornea incision (or optionally ringing back and forth between the two frequencies). When the aspiration ocular material is flowing at an expected flow rate that does not reflect an occluded or partially occluded aspiration pathway 121, the circuit 313 can drive the hollow titanium needle 106 to ring back at the ultrasonic frequency.

Some embodiments contemplate identifying the presence of a particle 590 either occluding or partially occluding the aspiration path 121 based on a diminishing change in irrigation flow rate of irrigation fluid into the eye 120. A sensor (not shown) can be located in the infusion/irrigation pathway 118, or elsewhere, to sense a diminished flow rate of irrigation fluid into the eye 120. Shifting ringing the hollow titanium needle 106 from an ultrasonic frequency to a high-ultrasonic frequency can help break apart an occluding particle 590 and reduce heating at the cornea incision (or optionally ringing back and forth between the two frequencies). When the infusion/irrigation pathway 118 is flowing irrigation fluid at an expected flow rate that does not reflect an occluded or partially occluded aspiration pathway 121, the circuit 313 can drive the hollow titanium needle 106 to ring back at the ultrasonic frequency.

Some embodiments contemplate identifying the presence of a particle 590 either occluding or partially occluding the aspiration path 121 based on an increase in vacuum pressure (negative pressure) generated by the aspiration pump 154 (such as by back electro-magnetic force (EMF) of the pump or an inline sensor, for example) above what is considered a normal resistance to flow. Shifting ringing the hollow titanium needle 106 from an ultrasonic frequency to a high-ultrasonic frequency can help break apart an occluding particle 590 and reduce heating at the cornea incision (or optionally ringing back and forth between the two frequencies). When the aspiration pump 154 is functioning at an expected vacuum level that does not reflect an occluded or partially occluded aspiration pathway 121, the circuit 313 can drive the hollow titanium needle 106 to ring back at the ultrasonic frequency.

Some embodiments contemplate identifying the presence of a particle 590 either occluding or partially occluding the aspiration path 121 based on an increase in mass of the hollow titanium needle 106 due to a particle engaged therewith in an occluding/partially occluding manner. The transducer 116, for example, can be used to sense an increase in mass of the hollow titanium needle 106 due to an engaged particle based on an increase in voltage load to drive the frequency via the transducer 116. Shifting ringing the hollow titanium needle 106 from an ultrasonic frequency to a high-ultrasonic frequency can help break apart an occluding particle 590 and reduce heating at the cornea incision (or optionally ringing back and forth between the two frequencies). When the mass of the hollow titanium needle 106 returns to a level that does not reflect an increased mass of the hollow titanium needle 106, the circuit 313 can drive the hollow titanium needle 106 to ring back at the ultrasonic frequency.

Certain embodiments of the present invention contemplate employing frequencies ringing the hollow titanium needle 106 in a manner vice versa to the above embodiments describing ultrasonic frequencies modulating to high-ultrasonic frequencies. For example, generally ringing the hollow titanium needle 106 at a high-ultrasonic frequency and then modulating the ringing to an ultrasonic frequency may improve breaking up an occluding particle 590. For example, an occlusion may be cleared faster at ultrasonic frequencies where cavitation effects are stronger and whereby larger bubbles are generated by lower ultrasonic frequency waves. In one illustrative example, the hollow titanium needle 106 can be made to ring at a high-ultrasonic frequency but then be made to ring at an ultrasonic frequency when the hollow titanium needle 106 becomes occluded. Once the hollow titanium needle 106 is no longer occluded, the hollow titanium needle 106 is then made to ring at the high-ultrasonic frequency.

Embodiments of the present invention contemplate ringing the hollow titanium needle 106 between the ultrasonic frequency range (20 KHz-100 KHz) and a sonic frequency range (less than 20 KHz). A sonic frequency, or frequency that is in the sound range, greatly reduces the heating effects of vibration on the hollow titanium needle 106. A sonically vibrating hollow titanium needle 106 is considered a "cold" needle because there is little risk of burning the incision site of the cornea. Much like the embodiments described herein that are directed to modulating the frequency ringing the hollow titanium needle 106 between an ultrasonic frequency and a high-ultrasonic frequency, the same embodiments are further contemplated using the condition where sonic frequency is substituted in place of the high-ultrasonic frequency. In other words, embodiments herein are further envisioned to modulate the hollow titanium needle 106 from ultrasonic frequency to sonic frequency when there is an occlusion or partial occlusion, or optionally when a surgeon wants to manually switch between ultrasonic and sonic frequencies, or optionally toggling between the two after a predetermined amount of time, for example.

Certain embodiments of the present invention contemplate employing frequencies ringing the hollow titanium needle 106 in a manner vice versa to the above embodiments describing ultrasonic frequencies modulating to sonic frequencies. For example, generally ringing the hollow titanium needle 106 at a sonic frequency and then modulating to an ultrasonic frequency to break up an occluding particle 590.

Figure 7A:
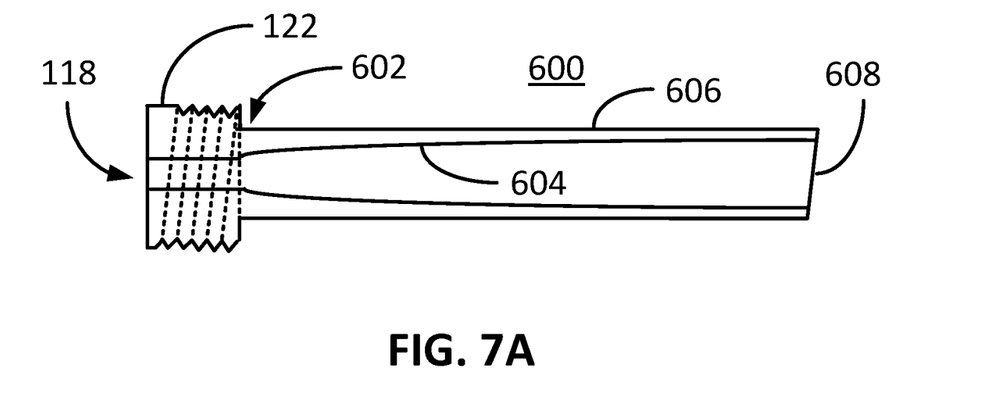
FIG. 7A-7D illustratively depict optional bore profiles in a hollow titanium needle consistent with embodiments of the present invention.
Figure 7B:
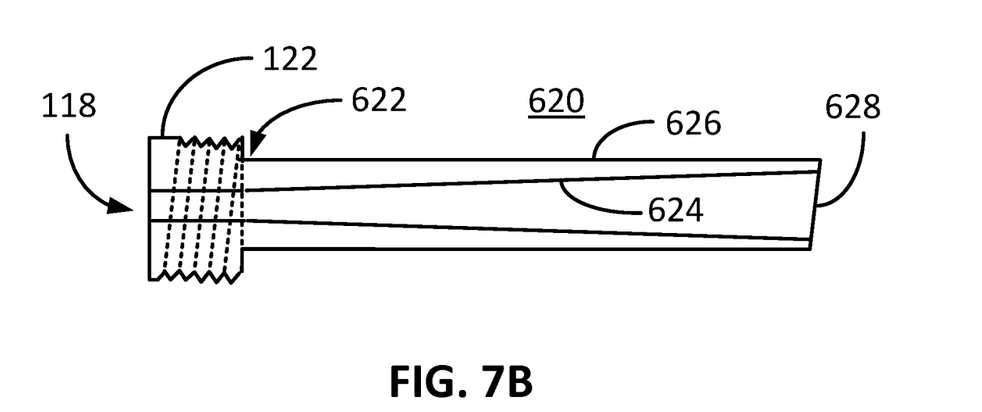
Figure 7C:
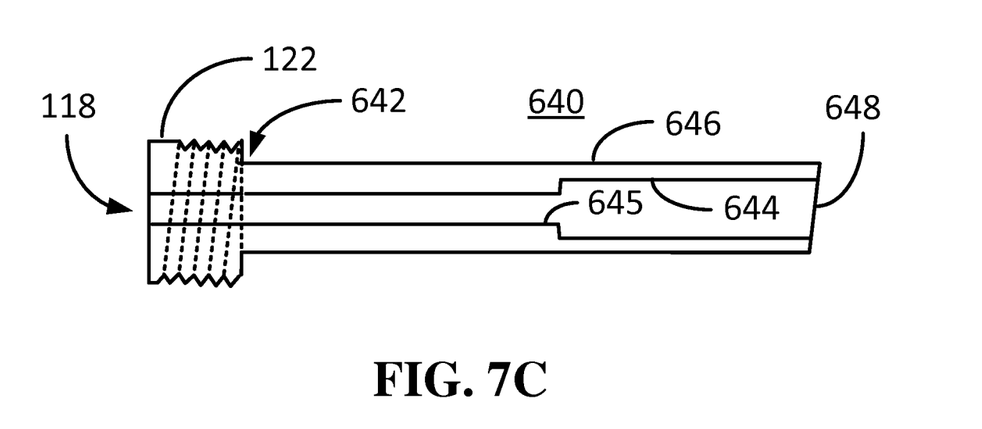
Figure 7D:
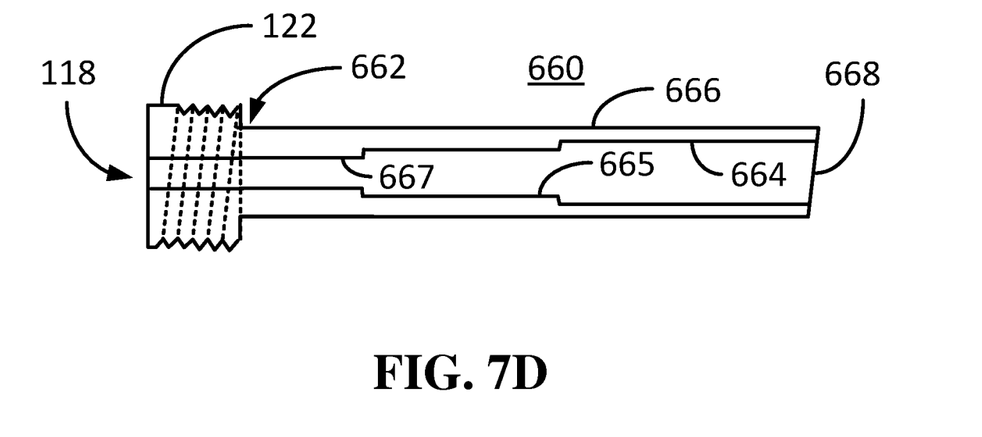

FIGS. 7A-7D contemplate alternate inner bore geometries wherein embodiments of the present invention can be practiced. FIG. 7A illustratively depicts a hollow titanium needle 600 comprising an elliptical shaped bore 604 that possesses a thicker needle wall as it approaches the supported end 602 and a thinner needle wall as it approaches the free distal tip 608. The outer needle diameter 606 is essentially consistent between the supported end structure 122 and the free distal tip 608. FIG. 7B illustratively depicts another embodiment of a hollow titanium needle 620 comprising an linear angulated bore 624 that possesses a thicker needle wall as it approaches the supported end 622 and a thinner needle wall as it approaches the free distal tip 628. The outer needle diameter 626 is essentially consistent between the supported end structure 122 and the free distal tip 628. FIG. 7C illustratively depicts yet another embodiment of a hollow titanium needle 640 comprising an internal stepped bore 644, 645 that possesses a thicker needle wall 645 proximal to the supported end 642 that steps to a thinner needle wall 644 as it approaches the free distal tip 648. The outer needle diameter 646 is essentially consistent between the supported end structure 122 and the free distal tip 648. FIG. 7D illustratively depicts yet another embodiment of a hollow titanium needle 660 comprising an internal stepped bore 664, 665, and 667 that possesses a thickest needle wall 667 proximal to the supported end 662 that steps to an intermediate thickness wall 665, than steps to a thinner needle wall 664 as it approaches the free distal tip 668. The outer needle diameter 666 is essentially consistent between the supported end structure 122 and the free distal tip 668. Though the step 645 in FIG. 7C and the steps 665 and 667 in FIG. 7D have thicknesses that are essentially parallel to the outer diameter of the hollow titanium needle 646 and 666, certain embodiments contemplate such a condition not required, wherein the thicknesses can be tapered, curved, etc., within the scope and spirit of different thickness bores. Moreover, the different thickness bores may be implemented to alter the frequency profile to create nodes of minimum amplitude or create varied frequency responses at specific locations along the length of the hollow titanium needle.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, though embodiments of the present invention describe modulating between a high-ultrasonic frequency and an ultrasonic frequency, it is contemplated that multiple ultrasonic frequencies and high-ultrasonic frequencies can be used while still maintaining substantially the same functionality without departing from the scope and spirit of the present invention. The specification and drawings are to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

It will be clear that the claimed invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the claimed invention disclosed and as defined in the appended claims. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. A surgical instrument for a phacoemulsification procedure, the surgical instrument comprising:
   a handpiece that includes a piezoelectric transducer;
   a hollow titanium needle having a free distal tip and a supported end structure that is attached to the handpiece, the supported end structure includes external threads that mate with internal threads in the handpiece, the hollow titanium needle having a substantially cylindrical portion between the supported end structure and the free distal tip;
   a circuit that drives the piezoelectric transducer to a) periodically expand and contract at a high-ultrasound frequency that rings the hollow titanium needle with a high-ultrasonic frequency standing wave consisting of a single node of minimum amplitude residing in the substantially cylindrical portion between the supported end structure and the free distal tip, and b) periodically expand and contract at an ultrasound frequency that rings the hollow titanium needle with an ultrasonic frequency standing wave, the circuit configured to switch the piezoelectric transducer from between the high-ultrasonic frequency and the ultrasonic frequency, but not both a) and b) at the same time.

2. The surgical instrument of claim 1 wherein the ultrasonic frequency has a range between 20,000 Hz and 100,000 Hz, and the high-ultrasonic frequency is above 100,000 Hz.

3. The surgical instrument of claim 1 wherein the circuit is adapted to switch between the high-ultrasonic frequency and the ultrasonic frequency after a predetermined time interval.

4. The surgical instrument of claim 3 wherein the predetermined time interval is set manually.

5. The surgical instrument of claim 1 wherein the circuit is adapted to switch between the high-ultrasonic frequency and the ultrasonic frequency via a manually operated switching device.

6. The surgical instrument of claim 1 wherein the circuit is adapted to switch from the ultrasonic frequency to the high-ultrasonic frequency during the phacoemulsification procedure when a rate at which ocular material passes through the hollow titanium needle slows, the circuit is further adapted to switch back to the ultrasonic frequency from the high-ultrasonic frequency when the rate at which the ocular material passes through the hollow titanium needle is no longer slowed.

7. The surgical instrument of claim 1 further comprising a vacuum pump that during the phacoemulsification procedure is adapted to withdraw ocular material from an eye through the hollow titanium needle at an established vacuum, the circuit adapted to switch from the ultrasonic frequency to the high-ultrasonic frequency when the established vacuum increases and back to the ultrasonic frequency when the established vacuum is no longer increased.

8. The surgical instrument of claim 1 wherein the circuit is adapted to switch from the ultrasonic frequency to the high-ultrasonic frequency when the circuit senses an increased load from a particle engaged with the hollow titanium needle in a way that does not pass through the hollow titanium needle and back to the ultrasonic frequency when the particle is either no longer engaged or the load is no longer increased.

9. The surgical instrument of claim 8 further comprising an irrigation sleeve possessing an irrigation port through which irrigation fluid can discharge inside of a eye at a flow rate during the phacoemulsification procedure, the irrigation sleeve enveloping a portion of the hollow titanium needle, the circuit adapted to switch from the ultrasonic frequency to the high-ultrasonic frequency when the flow rate decreases and back to the ultrasonic frequency when the flow rate is no longer decreased.

10. A method to drive oscillations in a surgical instrument during phacoemulsification, the method comprising:
    providing a handpiece that includes a piezoelectric transducer, a hollow titanium needle having a free distal tip and a supported end structure that is attached to the handpiece, the hollow titanium needle possessing a length being defined along a longitudinal axis of the hollow titanium needle;
    energizing the piezoelectric transducer to periodically longitudinally expand and contract at an ultrasonic driving frequency that rings the hollow titanium needle with an ultrasonic standing wave that is characterized by ultrasonic longitudinal expansion and contraction of the hollow titanium needle;
    inserting the hollow titanium needle in an eye; and then
    energizing the piezoelectric transducer to periodically longitudinally expand and longitudinally contract at a high-ultrasonic driving frequency that rings the hollow titanium needle with a high-ultrasonic standing wave that is characterized by high-ultrasonic longitudinal expansion and contraction of the hollow titanium needle, the standing wave characterized by less than a full wavelength that lies along the hollow titanium needle, the wavelength, the standing wave consisting of a single node of minimum amplitude along the length of the hollow titanium needle; and
    positioning the hollow titanium needle in the eye at approximately the node of minimum amplitude.

11. The method of claim 10 wherein the standing wave has a proximal node of minimum amplitude adjacent the supported end.

12. The method of claim 10 wherein the standing wave has a distal anti-node of maximum amplitude at the free distal tip.

13. The method of claim 10 further comprising switching between the ultrasonic driving frequency and the high-ultrasonic driving frequency after a predetermined amount of time.

14. The method of claim 10 further comprising switching from the ultrasonic driving frequency to the high-ultrasonic driving frequency when the hollow titanium needle becomes at least partially occluded.

15. The method of claim 10 further comprising switching from the high-ultrasonic driving frequency to the ultrasonic driving frequency when the hollow titanium needle becomes at least partially occluded.

16. The method of claim 10 further comprising switching from the ultrasonic driving frequency to the high-ultrasonic driving frequency when at least one of a) aspiration flow rate of ocular material aspirated from an eye slows through the hollow titanium needle; b) irrigation flow rate of irrigation fluid into the eye slows; c) an established vacuum for aspirating ocular material from the eye increases.

17. The method of claim 10 further comprising depressing a foot pedal that toggles the ultrasonic driving frequency to the high-ultrasonic driving frequency and back again.

18. A surgical instrument comprising:
    a phacoemulsification device possessing a handpiece and a hollow titanium needle, the hollow titanium needle possessing a supported end that is attached to the handpiece via external threads that mate with internal threads in the handpiece, the hollow titanium needle having a substantially cylindrical portion that extends from the supported end and terminates at a free distal tip; and a transducer that vibrates the hollow titanium needle with either an ultrasonic standing wave at an ultrasonic frequency or a high-ultrasonic standing wave at a high-ultrasonic frequency that is characterized by less than a full wavelength that lies along the hollow cylinder, the wavelength consisting of a single node of minimum amplitude residing in the substantially cylindrical portion between the supported end structure and the free distal tip.

19. The surgical instrument of claim 18 wherein the transducer is adapted to change vibration from the ultrasonic frequency to the high-ultrasonic frequency when at least one of a) aspiration flow rate of ocular material aspirated from an eye slows through the hollow titanium needle; b) irrigation flow rate of irrigation fluid into the eye slows; c) an established vacuum for aspirating ocular material from the eye increases.

20. The surgical instrument of claim 18 wherein the wavelength is essentially a three-quarter wavelength.

* * * * *